(12) United States Patent
Nguyen et al.

(10) Patent No.: US 6,550,323 B1
(45) Date of Patent: Apr. 22, 2003

(54) FATIGUE MACHINE FOR TESTING CORD OR FILAMENT

(75) Inventors: Gia Van Nguyen, Rossignol (BE); Florence de Boisfleury, Bourscheid (LU); Jean Luc Dheur, Arlon (BE)

(73) Assignee: The Goodyear Rubber & Tire Company, Akron, OH (US)

( * ) Notice: Subject to any disclaimer, the term of this patent is extended or adjusted under 35 U.S.C. 154(b) by 0 days.

(21) Appl. No.: 09/513,630

(22) Filed: Feb. 28, 2000

(51) Int. Cl.[7] .............................. G01L 5/04; G01N 3/08
(52) U.S. Cl. .............................. 73/158; 73/160; 73/826
(58) Field of Search ........................... 57/902, 212, 200; 73/7, 781, 808, 158, 849, 810, 834, 851, 144, 862.45, 159, 826, 831, 160; 75/175.5; 324/718

(56) References Cited

U.S. PATENT DOCUMENTS

| | | | | |
|---|---|---|---|---|
| 3,943,761 A | * | 3/1976 | Shoberg et al. | 73/144 |
| 4,158,283 A | * | 6/1979 | Nation | 57/200 |
| 4,403,499 A | * | 9/1983 | Sack et al. | 73/7 |
| 4,452,065 A | * | 6/1984 | Minter | 73/7 |
| 4,534,228 A | * | 8/1985 | Burbank, Jr. | 73/862.45 |
| 5,952,836 A | * | 9/1999 | Haake | 324/718 |

* cited by examiner

Primary Examiner—Max Noori
(74) Attorney, Agent, or Firm—David E Wheeler; Richard B. O'Planick

(57) ABSTRACT

An apparatus for testing the fatigue of a sample of cord or filament (12) by bending it over a fixed surface (19). The apparatus comprises a tensioner (14), a fixed bending surface (19) and a driving mechanism (24), whereby the driving mechanism (24) causes a non-twisting bending of cord or filament (12) over bending surface (19) while tensioner (14) maintains a constant tension on cord or filament (12). In a method of the invention, a cord or filament (12) is attached to a tensioner (14), the cord or filament (12) is mounted on fixed bending surface (19) and attached to non-stationary roller (20), and driving mechanism (24) is activated to cause a back and forth movement of roller (20), thereby causing filament or cord (12) to bend back and forth over fixed bending surface (19) until it breaks. This process is repeated using different stress increase rates on the cord or filament (12) by adjusting the tensioner (14) and a linear regression equation is used to determine the fatigue stress limit of the material.

10 Claims, 2 Drawing Sheets

FATIGUE MACHINE FOR TESTING CORD OR FILAMENT

TECHNICAL FIELD

The invention relates to an apparatus, which can be used for testing the fatigue properties of cords and filaments. The cords or filaments may be tested independently, or as part of a composite embedded in an elastomeric or plastic matrix.

BACKGROUND ART

Conventional apparatus for testing the fatigue properties of a filament or cord apply a constant load, while bending or reverse bending a sample of the filament or cord around one or more pulleys or rollers by using a reciprocating driving mechanism. When a reciprocating motion of a filament or cord is applied around pulleys or rollers, the bending load effects a given length of the sample instead of a localized area. When using a standard one or three roll apparatus, the samples subjected to fatigue testing are not subjected to a uniform number of cycles along their is length. The spreading out of the fatigue over this localized area leads to inaccurate fatigue results. The shorter the length of sample, the more accurate will be the results of the test, which will better represent the actual properties of the material.

An important characteristic of the fatigue performance of a material is its fatigue limit. In the prior art, fatigue limit is determined using numerous test at constant stress amplitude. The constant stress amplitude is progressively reduced to localize the fatigue limit. When the limit is approached, the length of time needed to run the standard fatigue test increases accordingly, and such tests are becoming increasingly expensive. Furthermore, close to the fatigue limit, dispersion becomes high and the number of tests for each level of stress amplitude has to be increased to make the determination statistically valid.

Fatigue failure is due to repetitive stresses. The relation between the maximum level of stress S of the repetitive stresses and the number of cycles N is represented by $$S=f(\log N),$$

i.e S is a function of the logarithm of N

Where S represents the constant stress amplitude, and N represents the number of cycles to failure.

As S is decreased to the fatigue limit, N increases infinitely. If the cord is maintained below this stress limit, the material will never fail due to fatigue.

It is an object of fatigue testing to determine the fatigue stress limit of a material. In prior art fatigue tests, where steel filaments or cables are tested, for example, the tests are done using a constant level of stress, and a constant cycling time for the repetitive flexing. Also, when steel cables are tested, the steel filaments used to make the cable are in contact with each other, and their movement relative to each other causes the filaments to fret. The fretting may cause the cord, cable of filament to break prematurely, and may give erroneous fatigue data. This fretting is significant, however, only at a large number of cycles, and is negligible at a low number of cycles.

It is an object of this invention to reduce the number of test cycles in fatigue testing.

It is also an object of this invention to provide an apparatus for testing the fatigue properties of a filament or cable which provides more accurate, reproducible results, and minimizes the amount of time needed to obtain the results.

Other objects of the invention will be apparent from the following description and claims.

SUMMARY OF THE INVENTION

An apparatus for fatigue testing cord, cable or filamentary material comprises (a) a tensioner (14) for controlling the tension of a cord, cable, or filament (12) to be tested, whereby a first end of the cord, cable or filament (12) is attached to the tensioner (14), (b) a rolling mechanism (30) directly or indirectly attached to said tensioner (14) by cord, cable, or filament (12) for bending the cord, cable, or filament (12), the rolling mechanism (30) comprising a stationary roller (18) and non-stationary roller (20), wherein the non-stationary roller (20) rides against the stationary roller (18), and (c) a crank arm (22) connecting the non-stationary roller (20) to a rotating driving mechanism (24), whereby the crank arm (22) is attached to the driving mechanism (24) at a perimeter thereof, and when the driving mechanism (24) rotates, the crank arm (22) causes the non-stationary roller (20) to move back and forth.

The illustrated apparatus further comprises a bending surface (19) attached to the stationary roller (18) wherein the back and forth movement of the non-stationary (20) roller causes a cord, cable or filament (12) that is to be tested to bend back and forth on the stationary bending surface (19), and a first attachment mechanism (15) for connecting a first end of a cord, cable or filament (12) to be tested to the tensioner (14), and a second attachment mechanism (17) for connecting a second end of a cord, cable or filament (12) to be tested to the non-stationary roller (20).

In an illustrated embodiment, a method for testing the fatigue properties of a cord cable or filament comprises the steps of (a) attaching a first end of the cord, cable or filament (12) to a tensioner (14) to apply a first known and constant or constantly increasing tension to the cord, cable or filament (12) while testing, (b) mounting the cord, cable or filament (12) on a bending surface (19), (c) connecting a second end of the cord, cable or filament (12) to a non-stationary roller (20) that moves in a constant, non-twisting back and forth motion relative to the bending surface (19), (d) causing the non-stationary roller (20) to move back and forth until the cord, cable or filament (12) breaks, (e) determining the fatigue limit by repeating steps (a) through (d) with different constantly increasing tensions by adjusting tensioner (14), and (f) using the data collected and a linear regression equation to calculate the fatigue stress limit of the material.

DETAILED DESCRIPTION OF THE INVENTION

Figure 1:
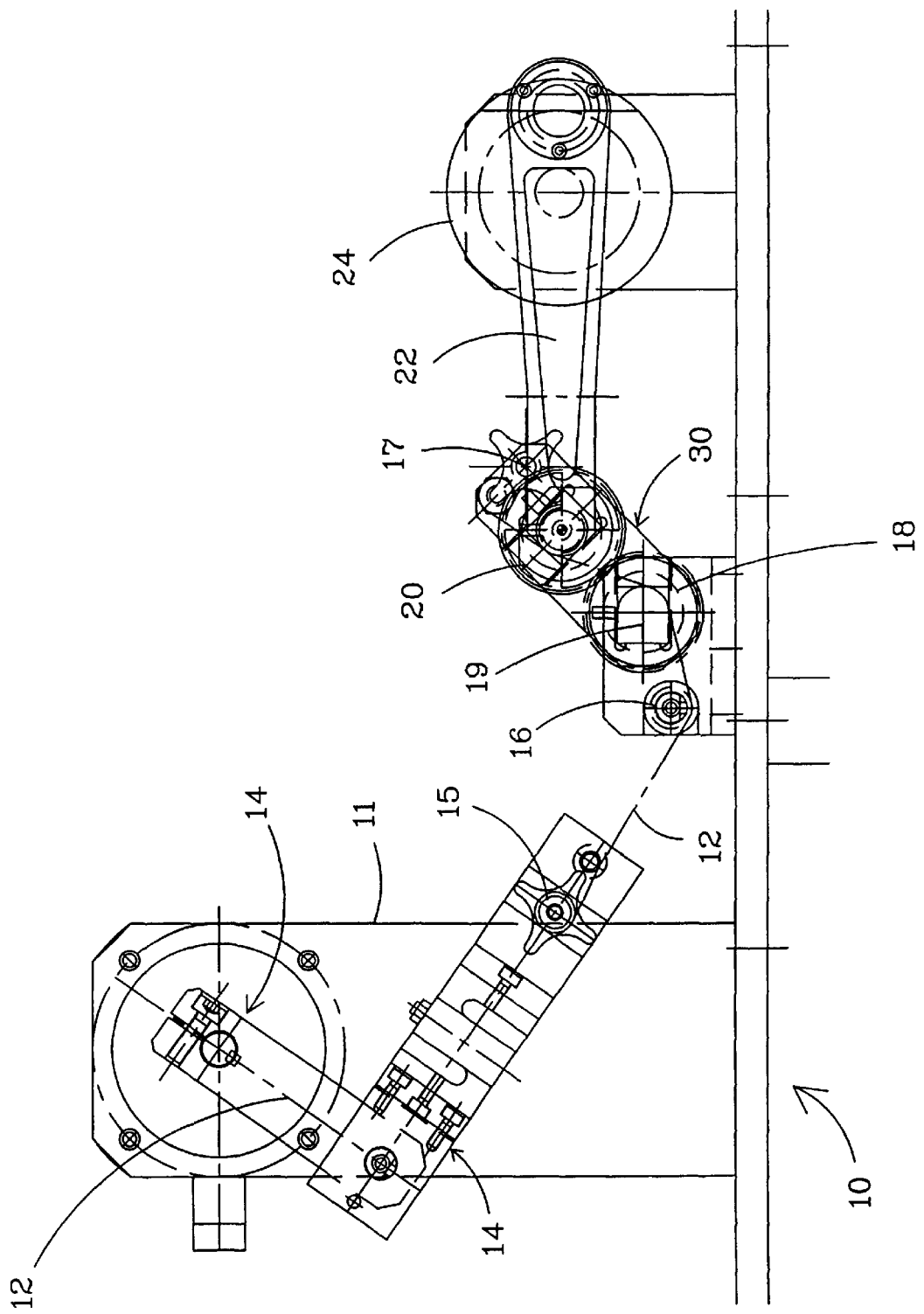
FIG. 1 illustrates a side view of the fatigue testing apparatus of the invention.
Figure 2:
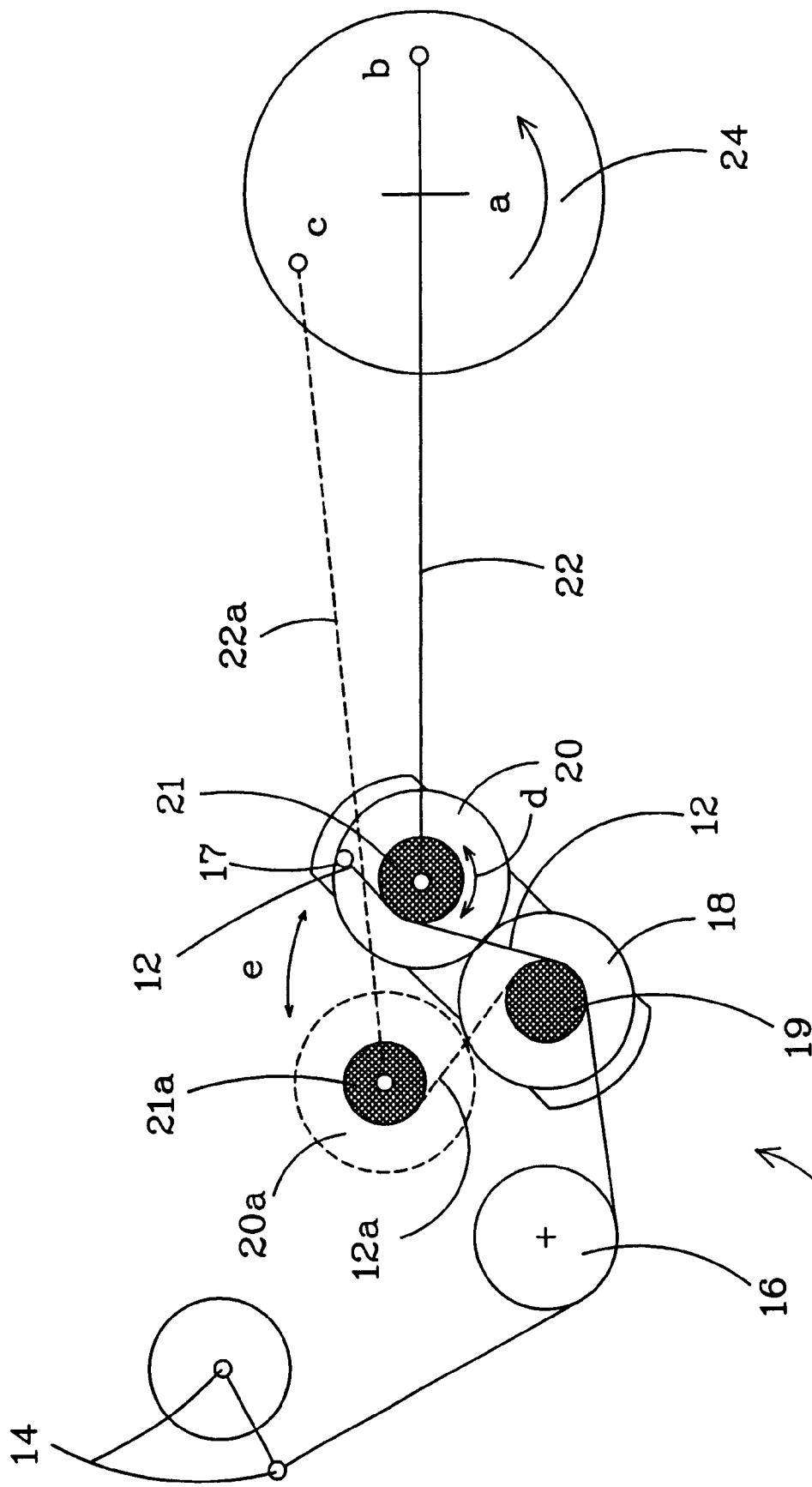
FIG. 2 illustrates a schematic of the operation of the fatigue testing apparatus of the invention.

With reference now to FIGS. 1 and 2, the apparatus 10 of the invention comprises a tensioner 14, attached to a stand 11, which is used to equilibrate the tension on the cord or filament 12 which is to be tested, so as to assure consistency of results. The sample of filament or cord 12 is attached to tensioner 14 via attachment mechanism 15, is wrapped over guide pulley 16 and over fixed bending surface 19, which is located on roller 18, and is attached to roller 20 at connection point 17. It is desirable that bending surface 19 be fixed, so that a particular point of cord or filament 12 is subjected to bending, and in the illustrated embodiment, roller 18 is fixed so that it does not rotate. Roller 18 and roller 20 comprise part of a rolling mechanism 30, which moves back and forth in a single plane because of the interaction of roller 18 and roller 20. Roller 20, whose circumference is contiguous with the circumference of roller 18, is rotatable back and forth in the direction of arrow 'd' on the circumference of the roller 18.

Tensioner 14 can be used to alter the tension on the cord or to keep it constant as required for the specific test being run.

Tensioner 14, in the illustrated embodiment, is electronically controlled, and can be used to constantly increase the stress applied to cord or filament 12 while being subjected to back and forth flexing against surface 19. The electronic control may be used to apply the stress increases in phase with the flexing cycles.

Guide pulley 16 is preferably rotatable. Guide pulley 16 is provided mainly to make possible a compact lay-out of the apparatus, and changes the direction of the test cord in a way that makes this possible. Tensions applied to cord 12 by tensioner 14 are transmitted through guide pulley 16 without modification.

Fixed bending surface 19 may have a diameter which can be varied depending on the severity of the bending stress required for a specific test. In the illustrated embodiment, bending surface diameter 19 may be varied from 2 mm to 30 mm, where diameters in the lower end of the range are preferred.

A first end of a crank arm 22 is connected to the center 21 of roller 20, and a second end of crank arm 22 is connected to a peripheral point 'b', 'c', of a driving wheel 24, which in the illustrated embodiment rotates in the direction of arrow 'a'. When the roller comprising drive mechanism 24 is disposed so that connecting point 'b' of crank arm 22 is in the right most position, roller 20 will be in a right most position relative to roller 18 and fixed bending surface 19. As the driving wheel 24 is rotated in the direction of arrow 'a', roller 20 rotates so that it moves to the left relative to roller 18 and fixed bending surface 19. As illustrated in FIG. 2, when the second end of crank arm 22 is rotated to position 'c', the first end of crank arm 22 is in the location 21a. The position of crank arm 22 is illustrated by dashed line 22a, whereby crank arm 22a has rotated roller 20 into a position illustrated by the phantom lines representing roller 20a. Accordingly, as the driving mechanism, represented by wheel 24 rotates, roller 20 rotates back and forth in the directions illustrated by arrow 'e', and the sample of filament or cord 12 bends around fixed bending surface 19 to the position illustrated by cord 12a.

Since the distance between the center of roller 18 and the center of roller 20 defines the length of sample being tested, and this distance always remains the same, and as roller 20 moves back and forth in the direction of arrow 'e', a fixed point on the sample is subjected to back and forth motion without any twisting or extraneous outside forces.

In the illustrated embodiment, fixed roller 18 and the roller 20 each have a diameter of about 60 mm. The illustrated driving mechanism 24 has a capability to rotate at about 3000 rpm.

Those skilled in the art will recognize that the concepts of this invention will apply to apparati having different dimensions and capabilities.

The apparatus includes computer controls and monitoring systems, not shown.

By analyzing the formula S=f(logN), Prot, "Memoires", Revue de Metallurgie, XLV, No. 12, 1948, generated a mathematical method whereby fatigue limits can be determined by constantly increasing the fatigue stresses on a material during testing. The Prot article is hereby incorporated herein by reference. The constant rate of increase Ri can be varied from one test to another, and a linear regression equation, using data obtained from samples of the same material tested while applying at least three different Ri, can be used to determine the fatigue limit of the material. For a valid linear regression, a series of 3 data points is a minimum, and a series of five is desirable. Statistically, 5 tests with at least three different Ri are preferred.

Using the apparatus of the invention, fatigue limits can be reached by increasing the stresses on a material, rather than using a large number of flexes. The tests are of shorter duration, thus eliminating error due to fretting, and saving laboratory time.

In the method of the invention, to determine the fatigue limit, a cord or filament to be tested is subjected to bending at a first constantly increasing stress until it breaks. At least two other rates of tension increase are used with other samples of the same material. A linear regression equation, using the at least three sets of data obtained, is used to calculate the fatigue stress limit of the material.

In the illustrated method of the invention, for testing the fatigue properties of a cord or filament 12, the method comprises the steps of (a) attaching a first end of the sample filament or cord 12 to a tensioner 14 to apply a first known and constantly increasing tension Ri to the sample during testing, (b) mounting the cord or filament 12 onto a bending surface 19, connecting a second end of a cord or filament to a non stationary roller 20 that moves in a constant, non-twisting back and forth motion relative to bending surface 19, and (c) activating a driving mechanism 24 which causes the non-stationary roller 20 to move back and forth, (d) continuing flexing until cord or filament 12 breaks, (e) repeating steps (a) through (d) using at least two more different constant rates Ri of increasing tension applied by tensioner 14, and (f) calculating the fatigue limit of the material using a regression equation and the data obtained from at least thee samples of the same material.

It is important that the level of bending, and the rate of additional stress levels applied to the bending cord be well monitored and controlled, and the method includes the further step of using computers to control the tensioner stresses and to monitor the test, and optionally to calculate the results.

What is claimed is:

1. An apparatus for fatigue testing cord, cable or filamentary material comprising:

(a) a tensioner (14) which is electronically controlled and used to constantly increase the tension of a cord, cable, or filament (12) to be tested, whereby a first end of said cord, cable or filament (12) is attached to said tensioner (14)

(b) a rolling mechanism (30) directly or indirectly connected to tensioner (14) by cord, cable, or filament (12) for bending said cord cable or filament (12), the rolling mechanism (30) comprising: a stationary roller (18) and a non-stationary roller (20), wherein the non-stationary roller (20) rides against said stationary roller (18)

(c) a crank arm (22) connecting said non-stationary roller (20) to a rotating driving mechanism (24), whereby said crank arm (22) is attached to said driving mechanism (24) at a perimeter thereof and when said driving mechanism (24) rotates said crank arm (22) causes said non-stationary roller (20) to move back and forth.

2. The apparatus of claim 1 further comprising a bending surface (19), attached to said stationary roller (18) wherein the back and forth movement of said non-stationary (20) roller causes a cord, cable or filament (12) to be tested to bend back and forth on said stationary bending surface (19).

3. The apparatus of claim 1 further comprising a first attachment mechanism (15) for connecting a first end of a cord, cable or filament (12) to be tested to said tensioner (14), and a second attachment mechanism (17) for connecting a second end of a cord, cable or filament (12) to be tested to said non-stationary roller (20).

4. A method for testing the fatigue properties of a cord, cable, or filament (12) comprising the steps of: (a) bending a first sample of a cord, cable or filament (12) at a first constantly increasing stress until it breaks, and (b) increasing the rate of increase of stress on at least a second sample of the cord, cable or filament and bending said at least second sample until it breaks, and a (c) using the data from the at least two samples and a linear regression equation to calculate the stress fatigue of the material.

5. The method of claim 4 comprising the steps of
 (a) attaching a first end of said cord, cable or filament (12) to a tensioner (14) to assure that a known and constantly increasing tension is applied to said cord, cable or filament (12) while testing,
 (b) mounting said cord, cable or filament (12) on a bending surface (19),
 (c) connecting a second end of said cord, cable or filament (12) to a non-stationary roller (20) that moves in a constant, non-twisting back and forth motion relative to said bending surface (19),
 (d) causing said non-stationary roller (20) to move back and forth until said cord, cable or filament (12) breaks,
 (e) repeating steps (a) through (d) using a at least one different sample of the same test material and a different constantly increasing tension applied by tensioner (14),
 (f) using a linear regression equation to calculate the stress fatigue resistance of cord or filament 12 using data collected from the at least two different samples.

6. The method of claim 5 wherein steps (a) through (d) are repeated using bending surfaces (19) having a different radii.

7. An apparatus for fatigue testing cord, cable or filamentary material comprising:
 means for bending a first sample of cord, cable or filament at a first constantly increasing stress until it breaks, and
 means for increasing the rate of increase of stress on at least a second sample of the cord, cable, or filament and bending the at least second sample until it breaks; and
 means for using data from the at least two samples to calculate stress fatigue of the material.

8. The apparatus of claim 7, wherein the means for bending the first sample comprises a rolling mechanism.

9. The apparatus of claim 7, wherein the means increasing the rate of increase of stress comprises a tensioner for increasing the tension of the cord, cable or filament.

10. The apparatus of claim 7, wherein the means for using data comprises a linear regression equation.

* * * * *